United States Patent
Cheng

[19]

[11] Patent Number: 5,939,313
[45] Date of Patent: Aug. 17, 1999

[54] STATIONARY VORTEX SYSTEM FOR DIRECT INJECTION OF SUPPLEMENTAL REACTOR OXYGEN

[75] Inventor: Alan Tat Yan Cheng, Livingston, N.J.

[73] Assignee: Praxair Technology, Inc., Danbury, Conn.

[21] Appl. No.: 08/928,474

[22] Filed: Sep. 12, 1997

[51] Int. Cl.⁶ ...................................................... C12M 3/00

[52] U.S. Cl. ..................................... 435/289.1; 435/286.7; 435/296.1; 435/818; 261/76; 261/84; 261/121.1; 422/225; 422/231

[58] Field of Search ............................... 435/286.7, 289.1, 435/296.1, 818; 423/659; 261/76, 83, 84, 121.1; 422/225, 231

[56] References Cited

U.S. PATENT DOCUMENTS

| | | | |
|---|---|---|---|
| 4,001,090 | 1/1977 | Kalina | 195/109 |
| 4,036,699 | 7/1977 | Quigg | 195/142 |
| 4,670,397 | 6/1987 | Wegner et al. | 435/289.1 |
| 5,356,600 | 10/1994 | Kiyonaga et al. | 422/234 |

*Primary Examiner*—David A. Redding
*Attorney, Agent, or Firm*—Stanley Ktorides

[57] ABSTRACT

A method for efficiently providing supplemental oxygen to a reaction mixture which is oxidized by or otherwise uses air, wherein the reaction mixture is agitated to create one or more stationary vortices, oxygen is injected into the reactor vessel at a stationary vortex, and air bubbles are circulated within the reaction mixture in the reactor vessel and outside the stationary vortex or vortices into which the oxygen is injected.

10 Claims, 1 Drawing Sheet

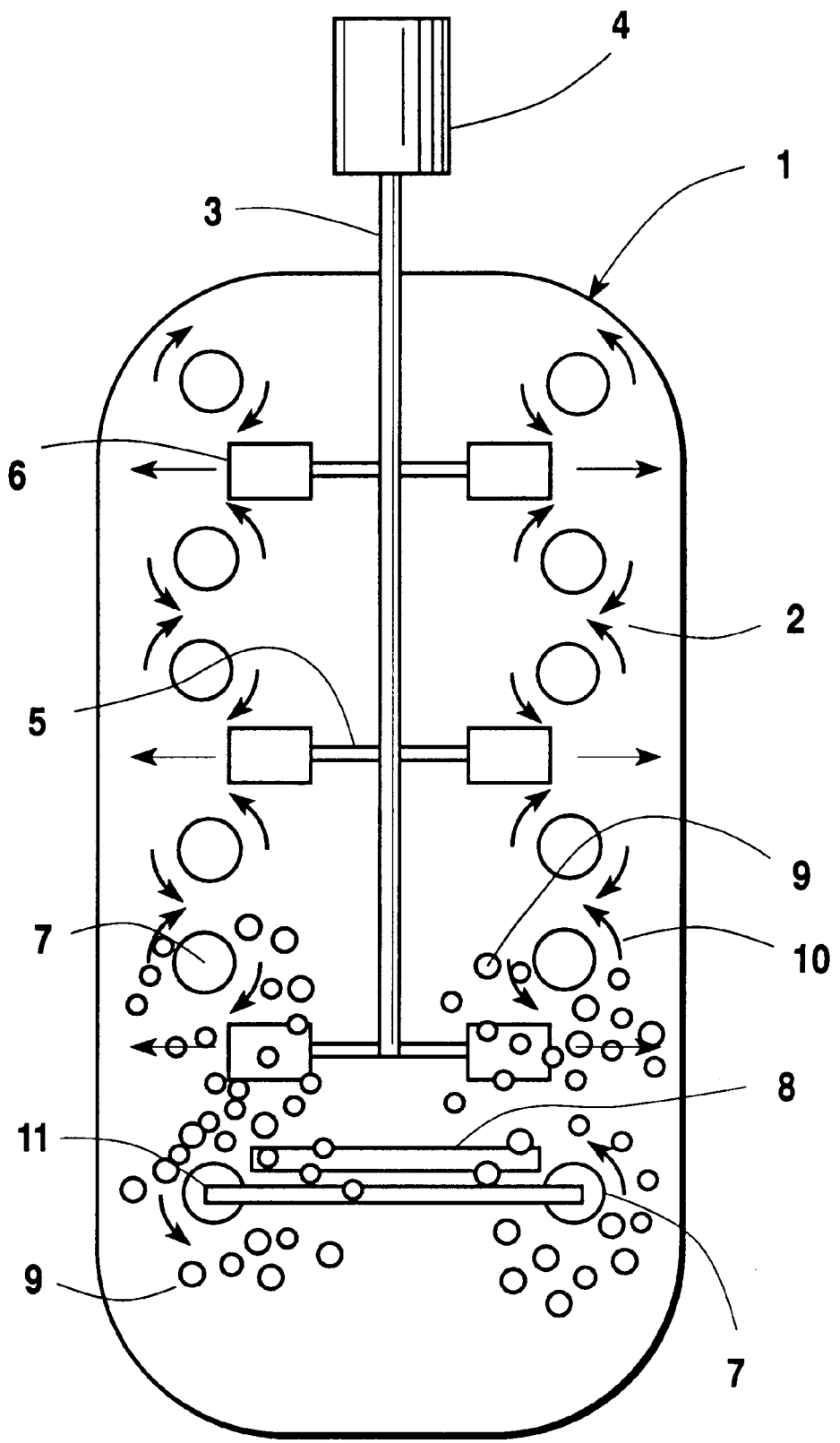

STATIONARY VORTEX SYSTEM FOR DIRECT INJECTION OF SUPPLEMENTAL REACTOR OXYGEN

TECHNICAL FIELD

This invention relates generally to reactions which use oxygen supplied by air, such as oxidation or fermentation reactions, and, more particularly, to such reactions which are carried out in an agitated reactor vessel.

BACKGROUND ART

In many organic oxidation and fermentation processes air is used to provide the source of oxygen. In order to increase the production rate, the air flow into the reactor vessel is increased and, in addition, the resulting air bubbles within the reaction mixture may be decreased in size, such as by the action of impellers or turbines. The increase in air flow into the reactor increases the amount of oxygen available for the oxidation or fermentation reaction, and the smaller size of the air bubbles increases the surface area to volume ratio of the air bubbles thus serving to increase the rate of oxygen mass transfer out from the air bubbles for dissolution in the reaction mixture and subsequent reaction.

However, there is limit to how much additional air may be passed into the reactor, because, beyond a certain flow, the impeller becomes flooded with gases.

To address this problem, oxygen is provided into the reactor to supplement the air. Because commercially available oxygen has an oxygen concentration several times that of air, a much lower volume of supplemental oxygen need be used, as opposed to the volume of additional air that would otherwise be needed, to provide a comparable level of additional oxygen to supplement the basic air. This helps to address the flooding problem, especially when the supplemental oxygen is provided into the reaction mixture at a distance from the impellers where the air is provided.

While air is relatively inexpensive, the use of oxygen imposes a higher cost to the oxidation or fermentation process. One way to moderate this higher cost is to improve the use efficiency of the supplemental oxygen. One way to achieve this is to reduce the tendency of the oxygen bubbles in the reaction mixture to coalesce with the air bubbles to form larger bubbles of oxygen-enriched air. Typically this is done by providing the supplemental oxygen into the reaction mixture at distance from where the air is provided into the reaction mixture.

It is thus seen that for several reasons commercial oxidation or fermentation reaction processes which employ oxygen to supplement air for reaction source oxygen, provide the oxygen into the reactor at a distance from where the air is provided and, consequently, at a distance from the impellers which are used to break up the air stream into smaller bubbles. Typically this supplemental oxygen is provided into the reaction mixture in a downflowing region within the reactor vessel to assure that it is provided far from the rising air bubbles.

While this conventional system effectively keeps the oxygen from coalescing with the air which would negate to a large extent the advantage of using the supplemental oxygen, this procedure has its own drawbacks. With the provision of supplemental oxygen into a reactor vessel at a distance from where the air is provided, the circulation effect within the vessel is reduced because of the braking action of the supplemental oxygen bubbles which try to rise within the downflowing region of the reaction mixture. This reduces the overall efficiency of the process. Moreover, even with a downward pumping impeller, oxygen bubbles can quickly escape to the reaction mixture surface in a turbulently mixed reactor. Thus, injecting the oxygen away from the bottom of the reactor where the air is introduced reduces the residence time available for the oxygen dissolution.

Accordingly, it is an object of this invention to provide an improved method for providing supplemental oxygen to a reaction mixture to which air is also provided for oxidation or fermentation purposes.

SUMMARY OF THE INVENTION

The above and other objects, which will become apparent to those skilled in the art upon a reading of this disclosure, are attained by the present invention which is:

A method for providing supplemental oxygen to a reaction mixture comprising:

(A) providing air into a reactor vessel containing a reaction mixture, and passing the air in the form of air bubbles within the reaction mixture;

(B) agitating the reaction mixture to create a stationary vortex;

(C) providing oxygen in the form of oxygen bubbles directly into the stationary vortex; and (D) passing oxygen out from the oxygen bubbles and dissolving oxygen into the reaction mixture.

As used herein, the term "oxygen" means a fluid comprising at least 70 mole percent oxygen molecules. As used herein, the term "stationary vortex" means a rotating body of liquid with little or no transverse or axial movements at the center point of the body. A stationary vortex is formed when a body of liquid is moved by a mechanical agitation system but is deflected into a steady rotational motion due to the restraining effect of reactor geometry. The stationary vortex does rotate, but its linear or tangential speed is low compared to the fast moving fluid induced by the impeller immediately outside the stationary vortex. A stationary vortex differs from other types of vortices in that it does not bound onto the liquid surface, the impeller or the baffles.

As used herein, the term "bottom" when referring to the reactor vessel means below the lowermost agitator of the reactor vessel.

BRIEF DESCRIPTION OF THE DRAWING

The sole FIGURE is a cross-sectional representation of one reactor vessel which may be used in the practice of this invention.

DETAILED DESCRIPTION

The invention may be advantageously employed to carry out a large number of oxidation or fermentation reactions. For example, in the case of a fermentation reaction, the reaction mixture or fermentation broth generally comprises water, a nutrient or fermentable, constituent such as corn syrup, molasses and glucose, and a biological agent such as bacteria, fungus and yeast. The fermentation mixture may also contain additives such as antifoam agents, nitrates, pH adjustment chemicals and the like. Fermentation products which can be produced by the method of this invention include antibiotics such as penicillin, erythromycin and tetracycline, organic chemicals such as ethanol, sorbitol and citronellol, organic acids such as citric acid, tartaric acid and lactic acid, amino acids such as L-lysine and monosodium glutamate, polysaccharides such as baker's yeast and xanthan gum, vitamins such as ascorbic acid and riboflavin, and other products including enzymes, insecticides, alkaloids, hormones, pigments, steroids, vaccines, interferon and insulin. The invention may also be used for liquid phase oxidation reactions, examples of which include the oxidation of toluene to benzoic acid, the oxidation of p-xylene to p-toluic acid, the production of hydrogen peroxide through the oxidation of hydroquinone, the oxidation of toluene to phenol, and the oxidation of paraxylene to terephthalic acid.

The invention will be described in detail with reference to the Drawing.

The FIGURE illustrates a reactor vessel 1 containing a reaction mixture 2 which comprises at least one constituent which reacts with or otherwise uses oxygen. The invention will find greater utility in those instances where the reaction mixture has a high viscosity, such as within the range of from 100 to 1500 centipoise although the invention may be used effectively with a reaction mixture having a viscosity as low as 0.5 centipoise. Preferably the viscosity of the reaction mixture is within the range of from 100 to 1000 centipoise. For simplicity the fluid input and output piping associated with reactor 1 is not illustrated.

The reaction mixture 2 within reactor 1 is agitated by means of a revolving agitator comprising longitudinal shaft 3 which rotates under power from motor 4. Connected to longitudinal shaft 3 are a plurality lateral spokes 5, and attached thereto are paddles or impellers 6. As the impellers rotate in a circular motion through the interior of the reaction vessel, the reaction mixture is pushed outward to the sides of the reactor vessel and inward toward the central axis of the reactor vessel. This lateral movement of the reaction mixture causes the formation of a small stationary vortex 7 above and below each impeller 6. The lateral movement of the reaction mixture also causes a longitudinal circulation of the reaction mixture, upward along the central axis and downward along the sides of reactor vessel 1.

Air is provided into the reactor vessel, preferably at the bottom of the reactor vessel, such as through sparger 8. In the case of radial flow impellers such as is illustrated in the FIGURE, the air bubbles 9 formed from sparger 8 are sucked immediately into the rotating impeller. As the large air bubbles pass by the laterally revolving impeller edges, they are broken into smaller bubbles. Typically the average diameter of the air bubble is within the range of from 1 to 10 mm. The smaller air bubbles pass into the reaction mixture upflow along the reactor vessel central axis and around the periphery of each stationary vortex due to the peripheral reaction fluid flow around each stationary vortex illustrated by peripheral flow arrows 10, then into the reaction mixture longitudinal circulatory flow. Oxygen molecules pass out from the air bubbles, and are dissolved into the reaction mixture where they react with or are otherwise used by one or more constituents of the reaction mixture. The entrainment of the air bubbles into the longitudinally circulating reaction mixture flowing at the center and the sides of the reactor vessel, and the peripheral flow 10 of the reaction mixture about each stationary vortex, keeps the majority, preferably substantially all, of the air bubbles from entering the stationary vortices. However some air, e.g. up to about 20 percent of the air, may enter a stationary vortex without causing detriment in the practice of this invention. Most preferably, substantially all of the air is kept from entering the stationary vortex or vortices into which the oxygen is injected.

Oxygen is injected into the reactor vessel, preferably at the bottom, such as through sparger 11, directly into one or more of the stationary vortices 7. The oxygen is injected into the stationary vortex in the form of oxygen bubbles having an average diameter which, preferably is equal to or smaller than the average diameter of the air bubbles, and, most preferably, is within the range of from 0.1 to 10 mm. Since the oxygen bubbles in the stationary vortex are not broken down into smaller bubbles by the impeller, the oxygen sparger nozzles must be smaller than the air sparger nozzles so that small oxygen bubbles are formed immediately upon the injection of the oxygen into the liquid. This is possible since the volume of oxygen required is always smaller than that of the air. Oxygen molecules pass out from the oxygen bubbles, are dissolved into the reaction mixture, and react with or are otherwise used by one or more constituents of the reaction mixture. By injecting the oxygen directly into the stationary vortex and maintaining the oxygen bubbles within the stationary vortex until substantially all of the oxygen molecules have dissolved into the reaction mixture, very little of the oxygen coalesces with air bubbles and thus the oxygen is delivered efficiently to the reaction mixture for use. The oxygen and the air may be provided into the reactor vessel proximate one another and, moreover, both may be provided at the bottom of the reactor vessel, without encountering the lowered efficiency or gas flooding problems heretofore experienced when either of these injection schemes were previously attempted.

The following is provided to exemplify the invention and to demonstrate the advantages attainable thereby. It is not intended to be limiting.

A 10,000 gallon reactor vessel, similar to that illustrated in the FIGURE, was employed to carry out a fermentation reaction to produce an antibiotic. In a first comparative example, the oxygen for the fermentation was supplied solely by air passed into the reactor at a flow rate of 1000 standard cubic feet per minute (scfm) as shown in Table I, Column A. In a second comparative example, the process was repeated and the air was supplemented with oxygen which was passed into the reactor mixed together with the air, as shown in Table I, Column B. In the example of the invention, the process was repeated but with the oxygen passed into the reactor spaced from the location where the air is provided, and directly into the lowermost stationary vortex, as illustrated in the FIGURE. Data for this example is shown in Table I, Column C.

TABLE I

|  | A | B | C |
|---|---|---|---|
| O$_2$ from Air | 210.0 scfm | 210.0 scfm | 210.0 scfm |
| Pure O$_2$ | 0.0 scfm | 110.0 scfm | 110.0 scfm |
| O$_2$ Vented | 179.3 scfm | 273.3 scfm | 256.1 scfm |
| O$_2$ Consumed | 30.7 scfm | 46.7 scfm | 63.9 scfm |
| Overall Efficiency | 14.6% | 14.6% | 20.0% |
| Pure O$_2$ Utilization | 0% | 14.6% | 30.2% |
| O$_2$ Uptake Rate | 34 mmoles/hr | 44 mmoles/hr | 60 mmols/hr |

As can be seen from the results presented in Table I, with the practice of this invention more than double the amount of oxygen molecules are reacted compared to the air only case with only about a 50 percent increase in the volume of gas passed into the reactor. Furthermore, compared to case B which provides the same amount of air and oxygen to the reaction mixture but in a conventional manner, the method of this invention enabled a 37 percent improvement in the amount of oxygen used in the reaction.

Although the invention has been described in detail with reference to a certain preferred embodiment, those skilled in the art will recognize that there are other embodiments of the invention within the spirit and the scope of the claims.

I claim:

1. A method for providing supplemental oxygen to a reaction mixture comprising:
   (A) providing air into a reactor vessel containing a reaction mixture, and passing the air in the form of air bubbles within the reaction mixture;
   (B) agitating the reaction mixture to create a stationary vortex;
   (C) providing oxygen in the form of oxygen bubbles directly into the stationary vortex; and
   (D) passing oxygen out from the oxygen bubbles and dissolving oxygen into the reaction mixture.

2. The method of claim 1 wherein the average diameter of the oxygen bubbles is less than the average diameter of the air bubbles.

3. The method of claim 1 wherein the reaction mixture has a viscosity within the range of from 100 to 1000 centipoise.

4. The method of claim 1 wherein both the air and the oxygen are provided into the reactor vessel at the bottom of the reactor vessel.

5. The method of claim 1 wherein the reaction mixture undergoes oxidation.

6. The method of claim 1 wherein the reaction mixture undergoes fermentation.

7. The method of claim 1 wherein substantially all of the air bubbles are kept from entering the stationary vortex into which the oxygen is injected.

8. The method of claim 1 wherein a plurality of stationary vortices are created.

9. The method of claim 8 wherein the plurality of stationary vortices are vertically spaced within the reactor vessel.

10. The method of claim 8 wherein oxygen is provided into more than one stationary vortex.

* * * * *